United States Patent [19]

Guigan

[11] Patent Number: 4,714,590

[45] Date of Patent: Dec. 22, 1987

[54] CONDITIONING STRIP FOR PERFORMING MEDICAL ANALYSES ON A SAMPLE OF LIQUID AND USING DRY REAGENTS

[76] Inventor: Jean Guigan, 9, rue Jean Mermoz, 75008 Paris, France

[21] Appl. No.: 840,614

[22] Filed: Mar. 17, 1986

[30] Foreign Application Priority Data

Mar. 26, 1985 [FR] France ............................. 85 04477

[51] Int. Cl.⁴ ...................... G01N 21/07; G01N 35/04
[52] U.S. Cl. ..................................... 422/102; 356/246; 356/427; 436/45; 422/61; 422/64; 422/72
[58] Field of Search ...................... 436/45, 47; 422/64, 422/72, 102, 61; 356/246, 427

[56] References Cited

U.S. PATENT DOCUMENTS

4,431,606 2/1984 Revillet et al. ..................... 356/246
4,557,600 12/1985 Klose et al. ......................... 356/427

Primary Examiner—Michael S. Marcus
Attorney, Agent, or Firm—Sughrue, Mion, Zinn, Macpeak & Seas

[57] ABSTRACT

A method for performing a series of analyses on a single sample after automatically diluting said sample. The method uses a cabinet supporting a set of mechanical, optical, and electronic units together with conditioning strip (100) containing dry reagents and a diluent. After receiving a sample to be analyzed, each strip is located on the cabinet in order to be subjected to a sequence of mechanical and optical operations. The method in accordance with the invention is simple enough to be performed by medical practitioners in their own consulting rooms or offices.

3 Claims, 27 Drawing Figures

CONDITIONING STRIP FOR PERFORMING MEDICAL ANALYSES ON A SAMPLE OF LIQUID AND USING DRY REAGENTS

The present invention relates to a method of performing medical analyses on a sample of liquid and using dry reagents, and also to apparatus for performing the method.

The aim of the present invention is to provide a method of analysis capable of being used on a very small sample of liquid, e.g. on a few microliters. This is particularly advantageous for medial analyses, since it then becomes possible, for example, to avoid taking blood from patients by means of syringes since a few drops of blood taken from the end of a finger will suffice.

The invention also aims to provide a method capable of performing most of the medical analyses that are currently requested (there are about 300 of them).

Finally, the invention seeks to provide a method which is cheap and simple enough to enable a medical practitioner to perform the method directly using a stored collection of conditioning strips containing dry reagents and a diluent.

SUMMARY OF THE INVENTION

The present provides a method of performing medical analyses on a sample of liquid and using dry reagents, the method comprising the use:
  firstly of logitudinal conditioning strips made of transparent plastic material and comprising a container closed by a lid, said container being compartmented in order to form:
    a receptacle for said liquid sample, said receptacle being in communication with an opening through said lid, and said opening being closed by a stopper, said receptacle being connected via a capillary duct to a calibrated cell, which is in turn connected to an overflow chamber;
    a tank for containing a diluent liquid situated beneath said calibrated cell and communicating via an orifice with the face of said container which is closed by said lid;
    a mixing vat situated at one end of said strip and communicating via respective capillary ducts with said calibrated cell and with said tank of diluent, all of said above-mentioned capillary ducts being parallel to the longitudinal side walls of said strip; and
    a series of reaction vats aligned along one of said longitudinal side walls, and suitable for containing respective solid reagents, said reaction vats being connected via respective capillary ducts to a common duct in communication via a capillary duct with said mixing vat and acting as an overflow duct terminating in a common overflow vat;
  and secondly of a cabinet comprising:
    a central turntable having a diametrically extending groove which is at least twice as long as one said strips; and which is wide enough to receive such a strip;
    a coplanar and coaxial peripheral rim around said central turntable, having radial housings for receiving a plurality of conditioning strips and suitable for being driven in rotation independently from said central turntable; and
    a diametrically extending gantry over the rotary assembly supporting optical means such as a photometer;
  wherein the method comprises the steps of:
    inserting a sample for analysis into said sample receptacle in a conditioning strip;
    placing said strip in a radial housing in said peripheral ring;
    displacing said strip in translation along a radius of said diametrically extending groove to cause said mixing vat to be located close to the center of said central turntable;
    performing a first centrifuging operation having the effect of filling said calibrated cell with said sample;
    shifting said strip in translation along said diametrically extending groove so that said mixing vat is located close to the periphery of said central turntable;
    performing a second centrifuging operation having the effect of filling said mixing vat with said sample and said diluent, and of mixing said liquids in said mixing vat;
    shifting said strip in translation along said diametrically extending groove into the same position as occupied for said first centrifuging operation;
    performing a third centrifuging operation having the effect of filling said reaction vats and said overflow vat from said mixing vat; and
    returning said strip to a radial housing in said peripheral ring, and observing the reactions in said reaction vats by means of said photometer, the results of the photometric measurements being transmitted to a programmed computer.

The present invention also provdes a conditioning strip for performing the above method, said strip being constituted by a container and a lid made of transparent plastic material, said container being compartmented in order to form:
  a receptacle for said liquid sample, said receptacle being in communication with an opening through said lid, and said opening being closed by a stopper, said receptacle being connected via a capillary duct to a calibrated cell, which is in turn connected to an overflow chamber;
  a tank for containing a diluent liquid situated beneath said calibrated cell and communicating via an orifice with the face of said container which is closed by said lid;
  a mixing vat situated at one end of said strip and communicating via respective capillary ducts with said calibrated cell and with said tank of diluent, all of said above-mentioned capillary ducts being parallel to the longitudinal side walls of said strip; and
  a series of reaction vats aligned along one of said longitudinal side walls, and suitable for containing respective solid reagents, said reaction vats being connected via respective capillary ducts to a common duct in communication via a capillary duct with said mixing vat and acting as an overflow duct terminating in a common overflow vat;

In a preferred embodiment said container is in the form of a one-piece molding together with a bottom, said one-piece molding defining, together with said lid, said sample receptacle, said calibrated cell and its associated overflow chamber, said mixing vats, said reaction vats, and said sets of capillary ducts, the bottom of said container including a cavity which, together with said bottom, defines said diluent tank.

Said reaction vats contain respective reagents in the form of pellets or of freeze-dried material, and said diluent tank contains a quantity of diluent.

The present invention also provides apparatus for performing the above method, said apparatus comprising a cabinet constituting a support table having a transparent lid, said support table being fitted with:
- a central turntable having drive means for causing it to rotate about a vertical axis and having a diametrically extending groove whose width is slightly greater than the width of a conditioning strip and whose radius is slightly longer than the length of such a conditioning strip;
- a peripheral ring which is coplanar and coaxial with said central turntable, said ring having means for rotating it slowly and independently of said central turntable, and having a plurality of radially extending housings for receiving conditioning strips; and
- a gantry passing over said peripheral ring and supporting mechanical means for shifting a conditioning strip in translation from a radial housing in said ring into said groove of said turntable, and vice versa, and also having a photometer with n read heads situated above the region of a housing in the ring which is intended to receive the n reaction vats of a strip;

said apparatus further including a central unit for controlling the above means.

BRIEF DESCRIPTION OF THE DRAWINGS

Implementations of the invention are described by way of example with reference to the accompanying drawings, in which.

MORE DETAILED DESCRIPTION

Figure 1:
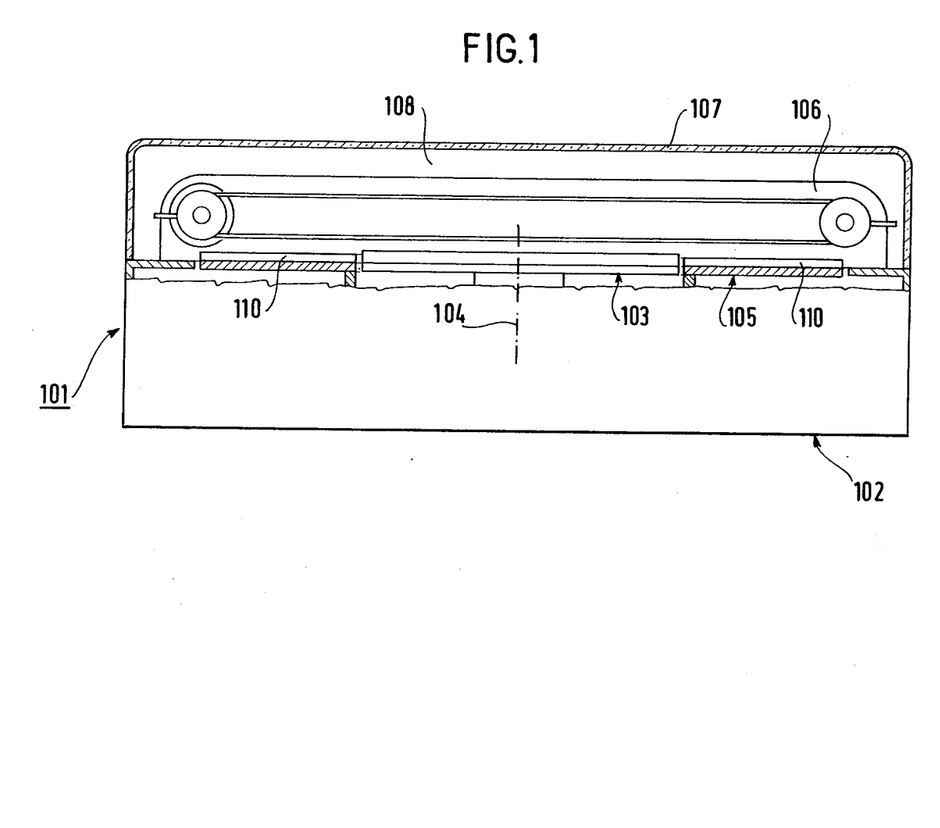
FIG. 1 is a diagrammatic elevation view in partial section through apparatus for performing the method in accordance with the invention.

FIG. 1 is a highly diagrammatically elevation in half section through apparatus for performing the method in accordance with the invention. The apparatus comprises a cabinet 101 including a support table 102 for a turntable 103 which rotates about an axis 104 and for a ring 105 which is substantially coplanar with the turntable and which is capable of rotating about the axis 104. A gantry 106 is fixed above this assembly and supports mechanical means and optical means which are described below.

The top of the support table 102 is covered by a transparent lid 107 which defines an enclosure 108 in which temperature conditions may be predetermined and held fixed, if so desired.

Figure 2:
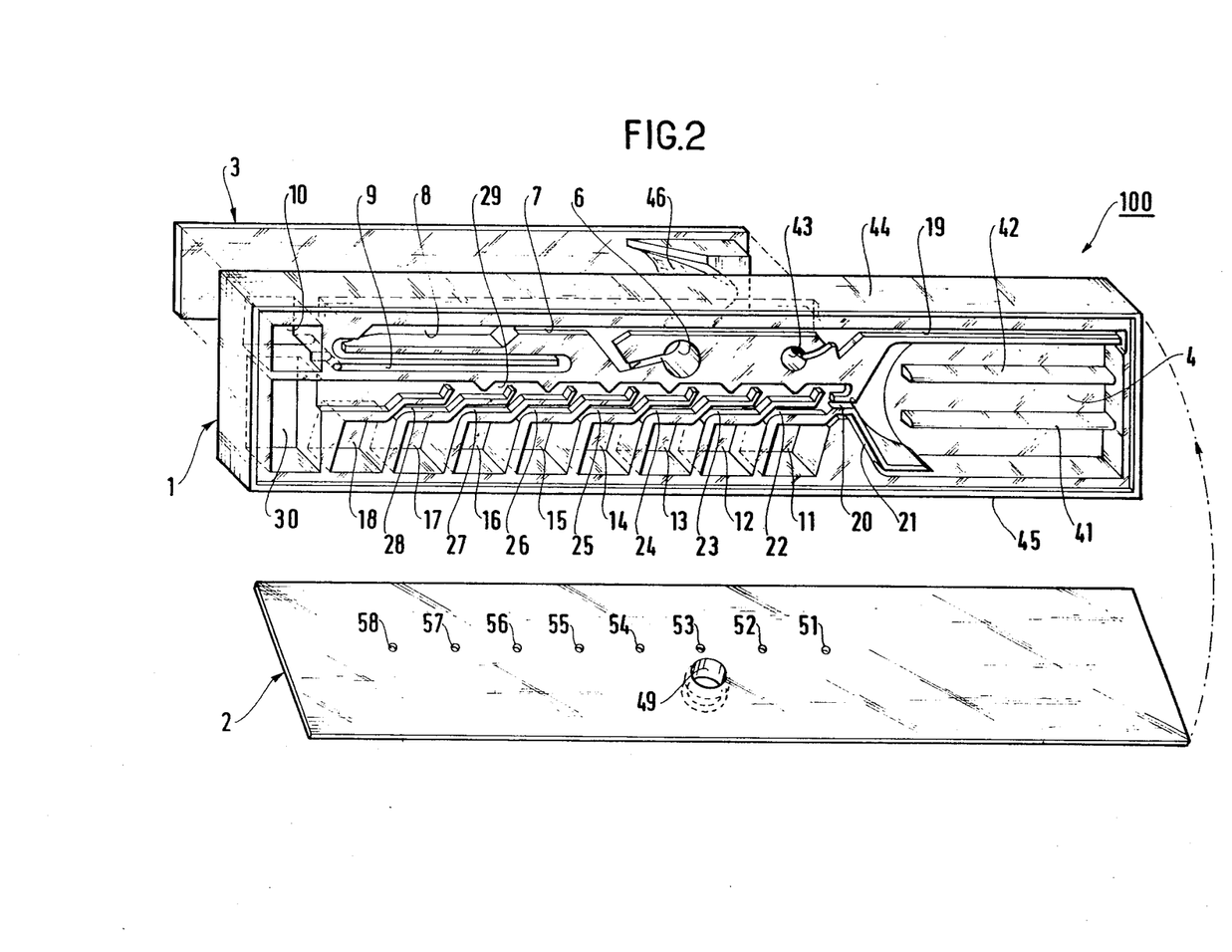
FIG. 2 is an exploded perspective view of a conditioning strip as used in the method in accordance with the invention, and as seen from the lid side.
Figure 3:
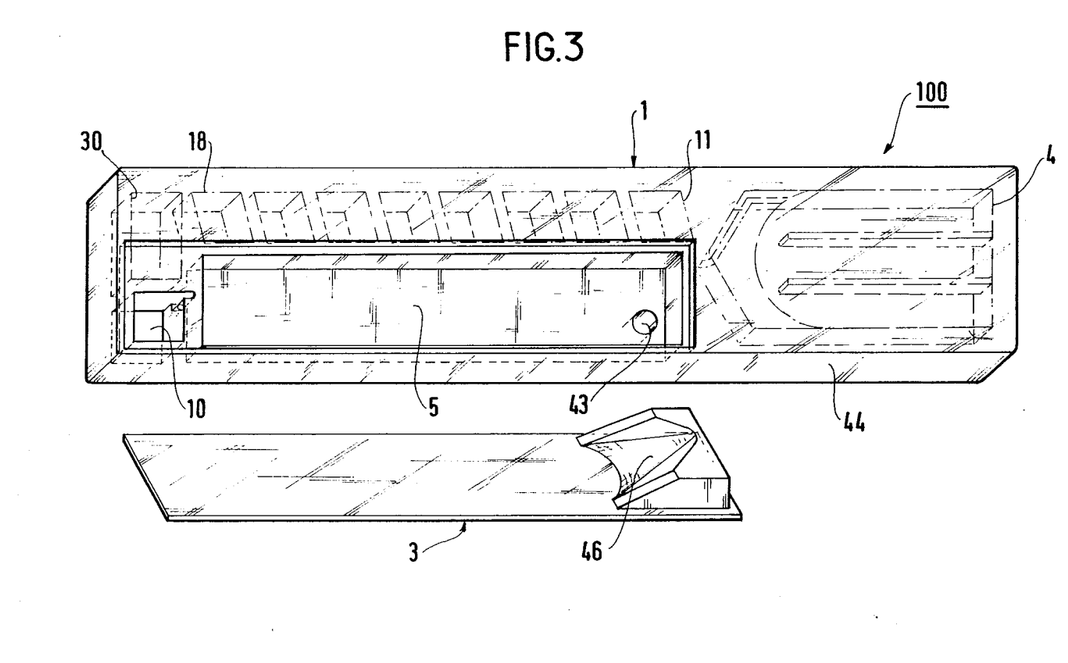
FIG. 3 is an exploded perspective view showing the bottom of the FIG. 2 strip.
Figures 4, 5:
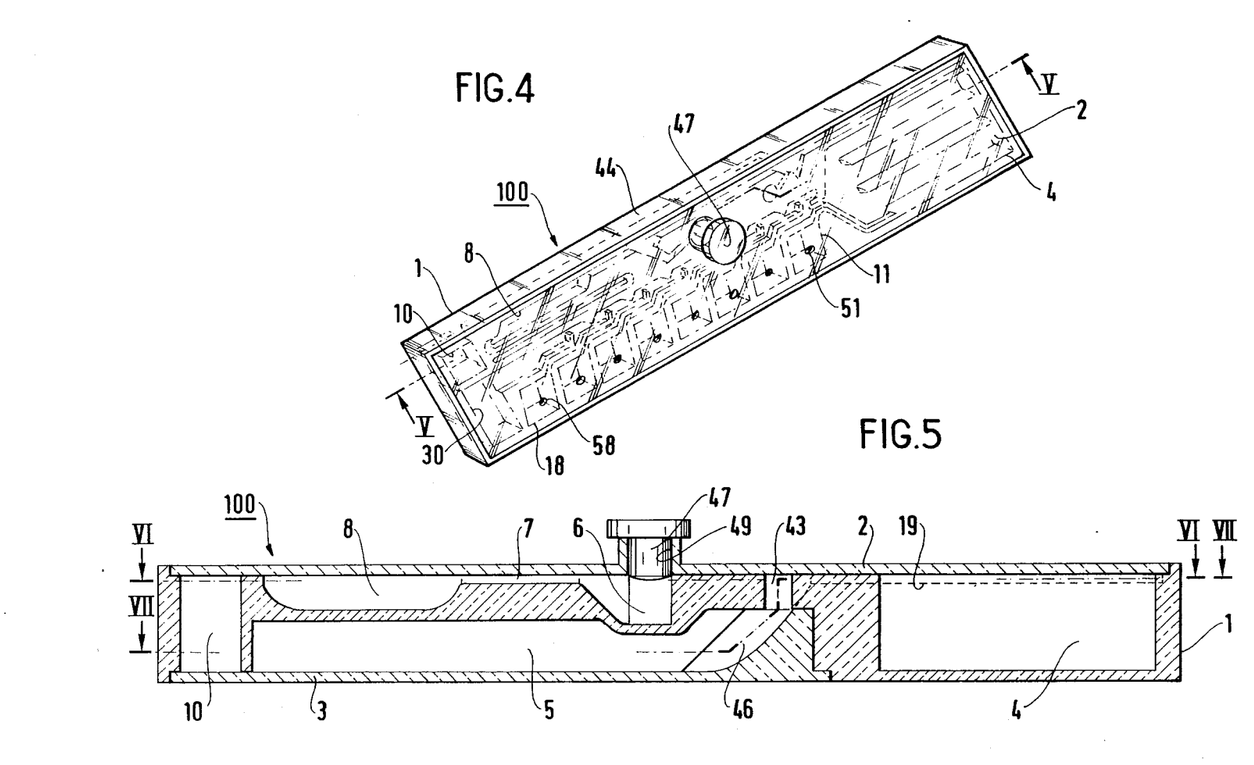
FIG. 4 is a perspective view of the strip shown in FIGS. 2 and 3.
FIG. 5 is a longitudinal section on a line V—V of FIG. 4.

The FIG. 1 apparatus is intended to receive a plurality of conditioning strips 100 of the kind shown in FIGS. 2, 3, and 4.

A strip 100 of transparent plastic material comprises a rectangular container 1 which is closed by a lid 2 and by a bottom wall 3. By way of example, the strip may be about 5 centimeters long and it may be about 1 centimeter high and 1 centimeter wide.

Adjacent to its longitudinal wall 44, the container 1 includes a receptacle 6 for a sample of liquid and in communication with an opening 49 through the lid 2. This receptacle is connected via a capillary duct 7 to a calibrated cell 8, which is in turn connected via a capillary duct 9 to an overflow chamber 10 and via capillary duct 19 to a mixing vat 4. The capillary ducts 7, 9, and 19 are parallel to each other and to the wall 44 of the container. They are situated near the top of the container and they are defined, in part, by the inside face of the lid 2.

A tank of diluent 5 is located underneath the capillary ducts 7 and 9 and the calibrated cell 8, and it can be seen clearly in perspective in FIG. 3. The tank is defined by the bottom 3 and a ramp portion 46 thereon when the container 1 is closed thereby. The tank 5 has an inlet orifice 43 visible in FIGS. 2 and 3. The capillary duct 19 leading to the mixing vat 4 opens out into the orifice 43. The mixing vat 4 is situated at the opposite end of the strip 100 to the calibrated cell 8 and is provided with a system of partial partitions consituted by two ribs 41 and 42 whose liquid-mixing function is explained below.

The mixing vat 4 also communicates with a series of reaction vats 11 to 18 running along the wall 45 of the strip 100. The reaction vat 11 communicates with the mixing vat 4 via a capillary duct 21 while the other reaction vats are fed via a common capillary feed duct 20 feeding individual capillary ducts 22 to 28. They also communicate with each other by means of a common overflow duct 29 which leads to a common overflow tank 30.

Vents 51 to 58 are provided through the lid 2 in association with each of the reaction vats 1 to 18.

FIGS. 4 and 5 clearly show how the calibrated cell 8, its overflow chamber 10, the tank of diluent 5 and the mixing vat 4 are arranged. the orifice 49 is closer by a stopper 47.

Figure 6:
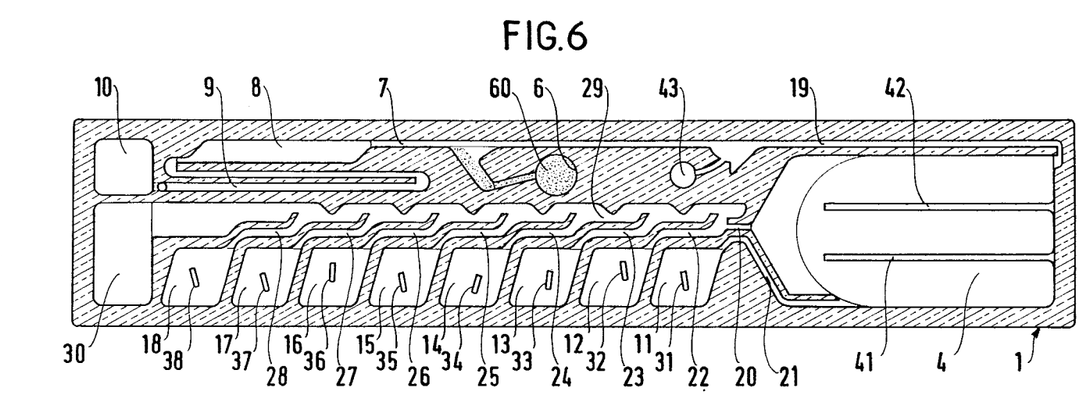
FIG. 6 is a section on a line VI—VI of FIG. 5.
Figure 7:
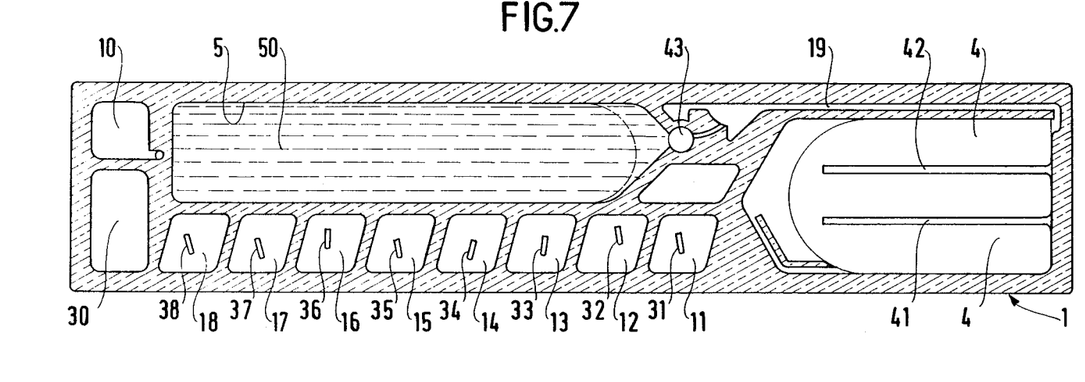
FIG. 7 is a section on a line VII—VII of FIG. 5.
Figure 8:
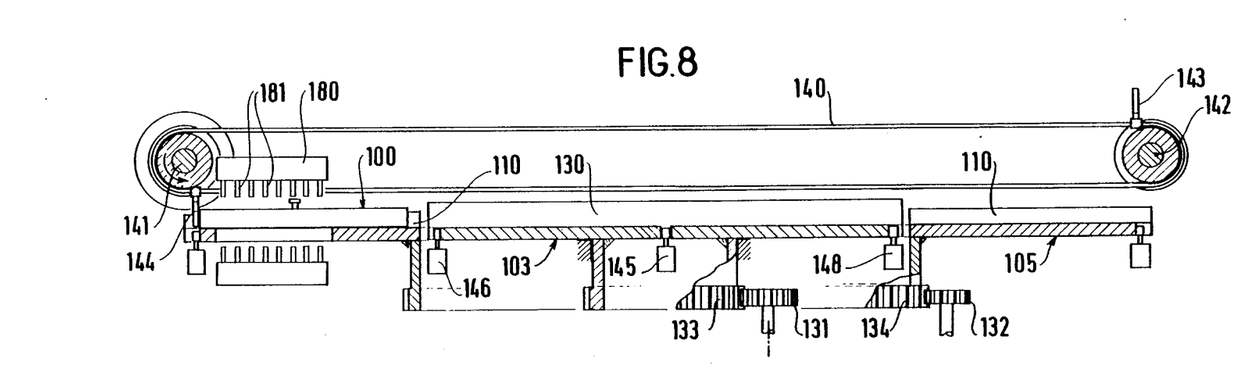
FIGS. 8 to 11 are diagrammatic cross-sections through the FIG. 1 apparatus containing a strip in accordance with the invention in various different positions.

In practice, the strips 100 are sold ready for use. In other words, as shown in FIGS. 6 and 7, the reaction vats 11 to 18 are provided with respective dry reagents 31 to 38, and the diluent tank is filled with diluent 50. The stopper 47 closes the orifice 49, and is removed when the strip is put into use in order to insert a quantity of liquid sample 60 for analysis (see FIG. 6).

For reasons which are explained below, the strip 100 is subjected to various movements on the turntable 103 or on the ring 105 of the cabinet shown in FIG. 1. The four main positions of the strip 100 are shown in FIGS. 8 to 11 where the apparatus is shown diagrammatically in section, and in FIGS. 12 to 17 where the same apparatus is seen from above.

The ring 105 has a plurality of radial housings 110 for receiving strips 100. For example, its outside diameter may be about 25 centimeters, and it may have about 30 housings. Drive means diagrammatically represented by two gear wheels 132 and 134 serve to rotate the ring 105 about the axis of symmetry 104 slowly and continuously, for example at 15 revolutions per minute.

The central turntable 103 has a diameter of about 12 cm, and may be rapidly rotated about its axis 104 by drive means diagrammatically represented by gear wheels 131 and 133. It also includes a diametriclaly extending groove 130 suitable for receiving a strip 100, together with pegs 145, 146, and 148 suitable for holding the strip in a first half or a second half of the groove 130.

A strip 100 is moved from a housing 110 in the ring 105 into the groove 130 of the turntable 103 by means of a mechanical chain system 140 driven by shafts 141 and 142 and provided with drive fingers 144 and 143. This mechanical strip-driving system is fixed to the gantry 106 on the cabinet 101.

The gantry 106 on the cabinet 101 further includes at least one optical device such as a photometer 180 provided with a n read heads 181 (e.g. eight read heads), situated above the ring 105 so as to be located above the eight reaction vats 11 to 18 of a strip 100.

The mechanical, optical, and electronic devices are operated under the control of a central control unit (not shown).

There now follows a deailed description of the various stages of the method in accordance with the invention.

A conditioning strip 100 provided with its sample 60 for analysis is initially in the stage illustrated in FIGS. 6 and 7. It is then inserted into a radial housing 110 in the ring 105 (see FIGS. 12) with its mixing vat 4 pointing towards the center of rotation. The ring 105 turns slowly and the housing 110 containing the strip 100 arrives level with the diametrically extending groove 130 of the turntable 103 (see FIGS. 13 and 8).

Figure 9:
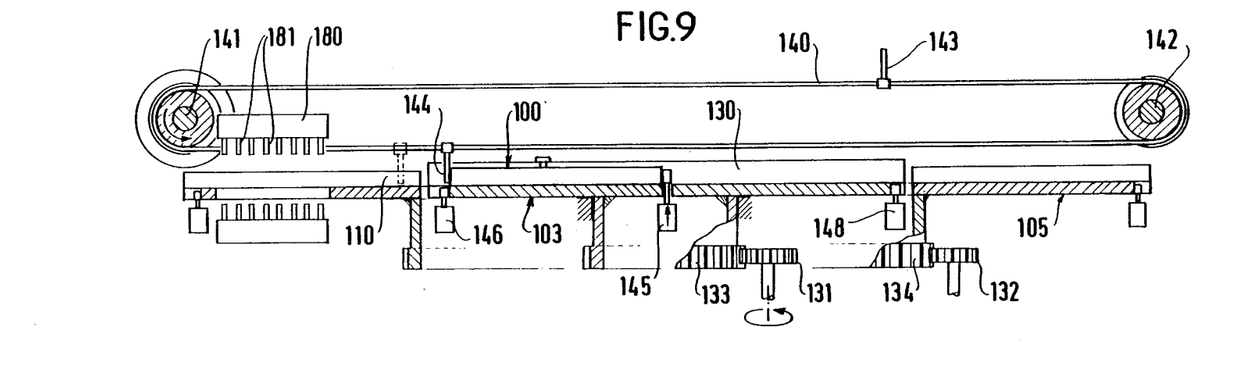
Figure 14:
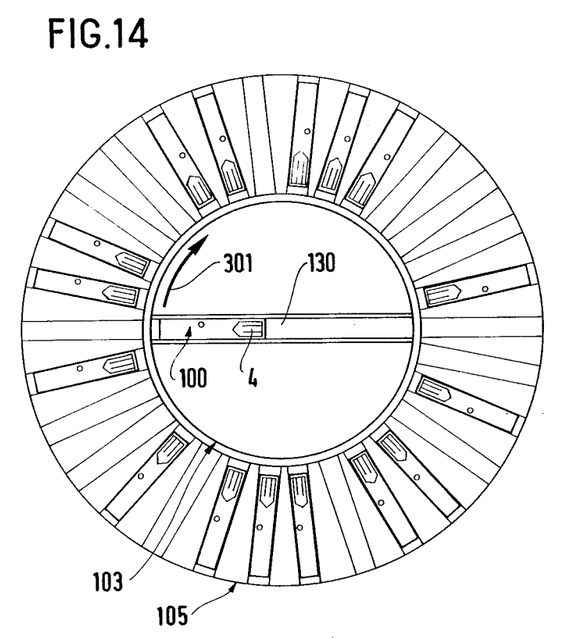

The strip 100 is driven by the finger 144 on the chain 140 into the groove 130 and its travel is stopped by the peg 145 (see FIGS. 9 and 14). The strip 100 is then centrifuged a first time as indicated diagrammatically by an arrow 301 in FIG. 14.

Figure 18:
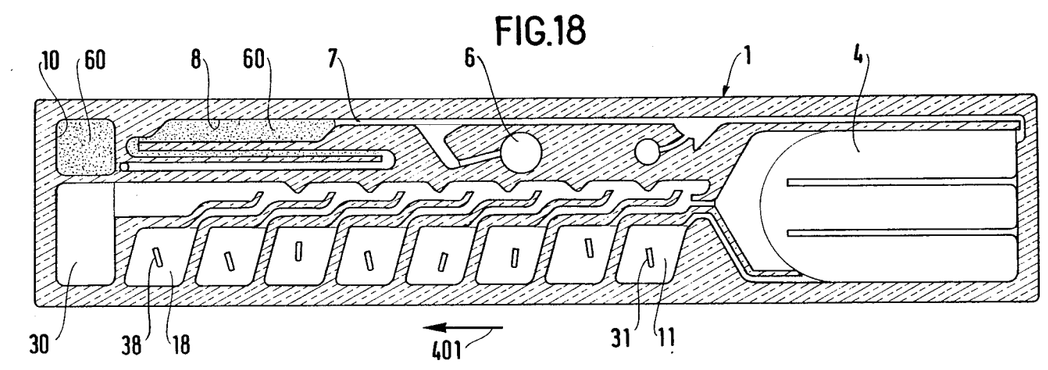
FIGS. 18 and 19 are views corresponding to FIGS. 6 and 7 respectively and show the stage of the method as illustrated by FIG. 14.
Figure 19:
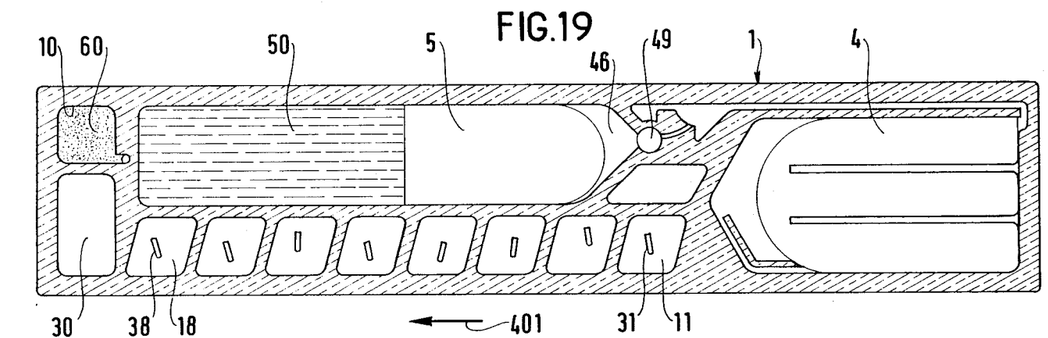
Figure 20:
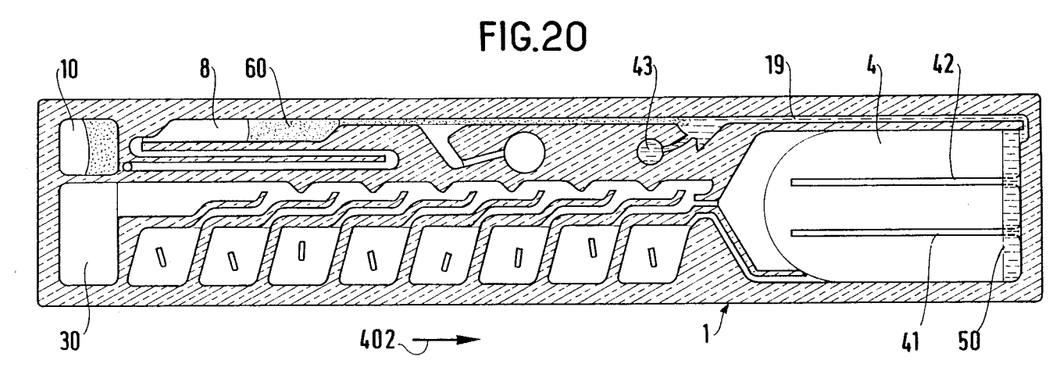
FIGS. 20 and 21 are analogous to FIGS. 18 and 19 respectively and show the stage of the method as shown in FIG. 15.
Figure 21:
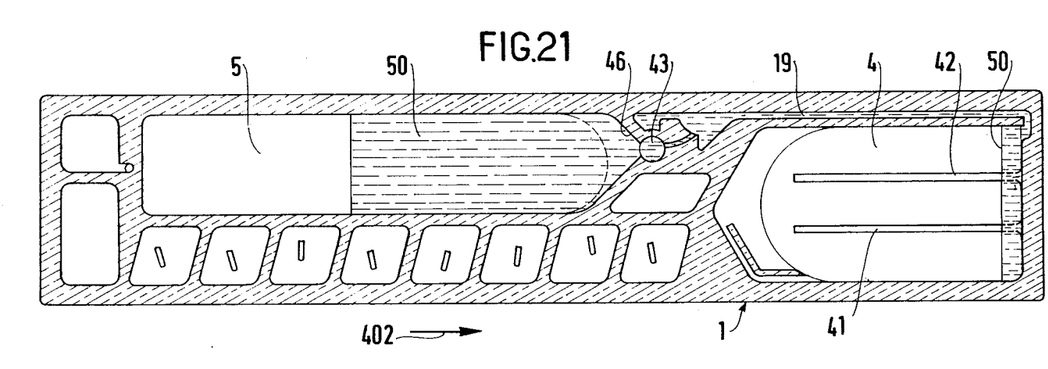
Figure 22:
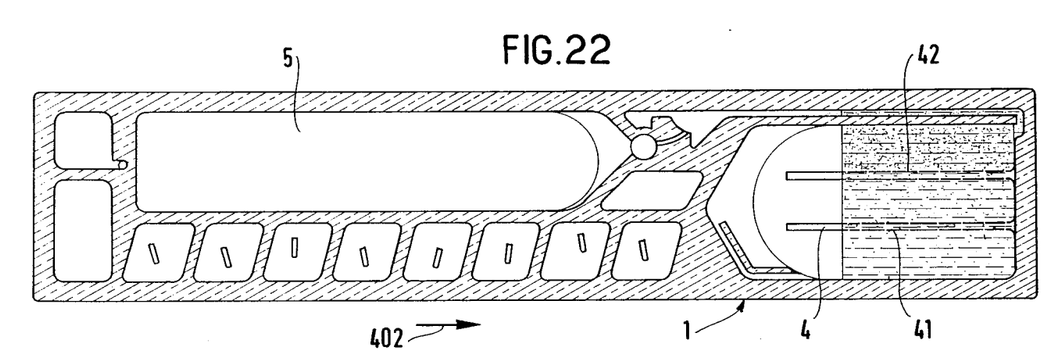
FIGS. 22, 23, 24, and 25 are similar views to FIG. 21 and show how the mixture changes during the stage of the method shown in FIG. 15.
Figure 23:
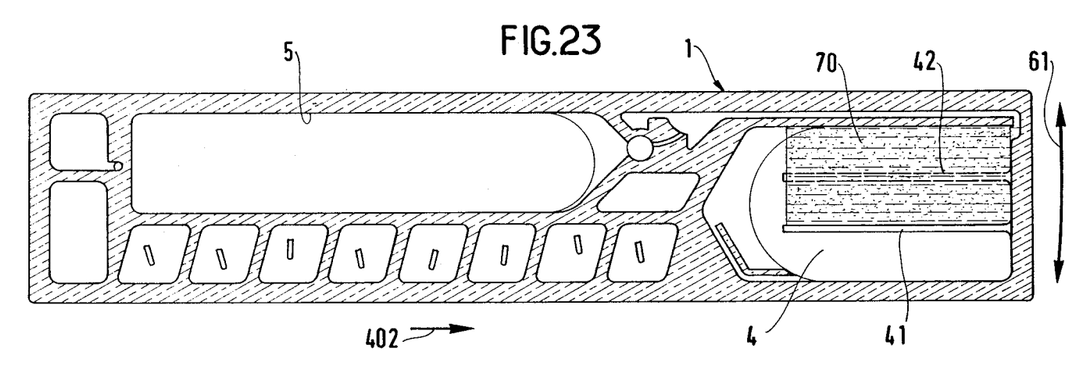
Figure 24:
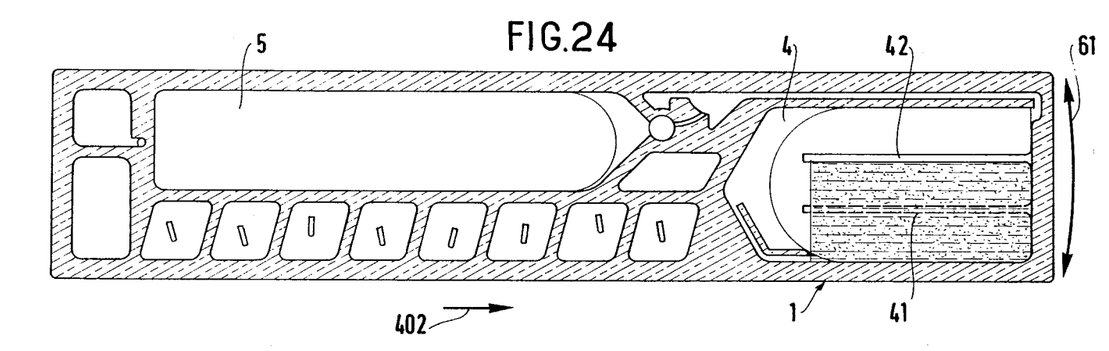
Figure 25:
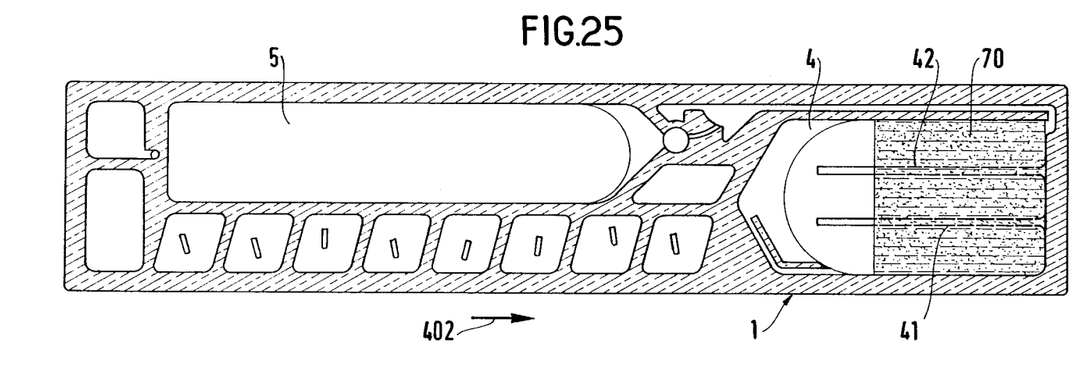

The distribution of liquids within the strip 100 during this first centrifuging operation can be seen in FIGS. 18 and 19, with arrow 401 indicating the corresponding direction of centrifugal force. The sample 60 shown by stipple shading passes from the receptacle 6 via the capillary duct 7 into the calibrated cell 8 and into its overflow chamber 10. The diluent 50, shown by dashed-line shading is kept in its tank 5.

Figure 10:
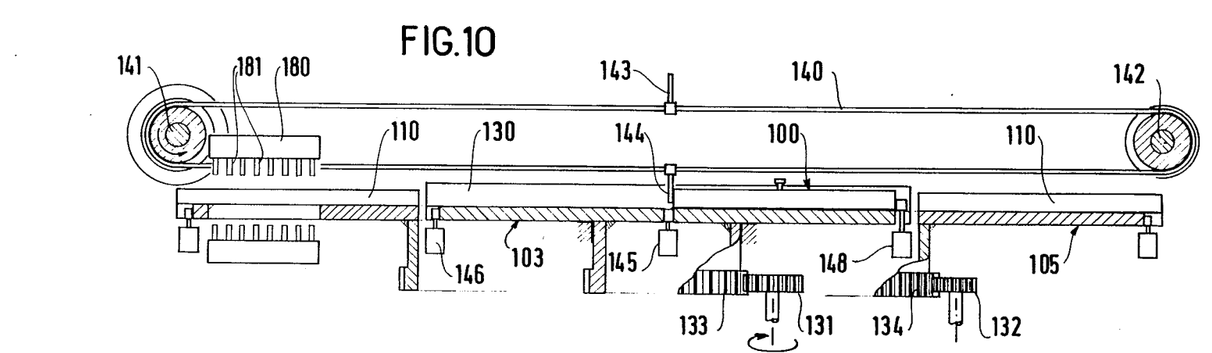
Figure 15:
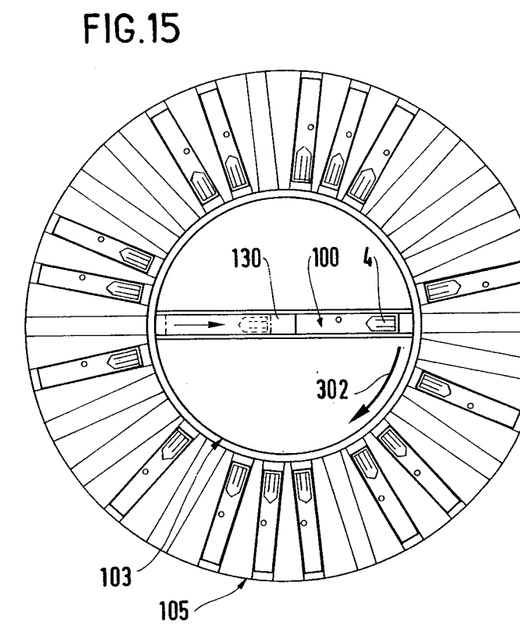

After the first centrifuging operation, the peg 145 is retracted and the strip 100 is driven by the finger 144 into the second portion of the diametrically extending groove 130 where it is held by the peg 148 (see FIGS. 10 and 15). The strip 100 is then subjected to a second centrifuging operation indicated diagrammatically by arrow 302.

FIGS. 20 to 25 show the effect of centrigugal force (as indicated diagrammatically by arrow 402) on the distribution of liquids in the strip 100. The sample 60 is expelled along the capillary duct 19 towards the mixing vat 4, while the diluent 50 is likewise expelled via the orifice 43 and the capillary duct 19 into the mixing vat 4.

In FIGS. 22 to 25, the two liquids entering the mixing vat 4 are mixed together by virtue of the partitioning ribs 41 and 42. This mixing is indicated diagrammatically by back-and-forth arrow 61. The mixing process is represented by the stipple dots (sample 60) spreading progressively throughout the dashed-line shading (diluent 50).

Figure 11:
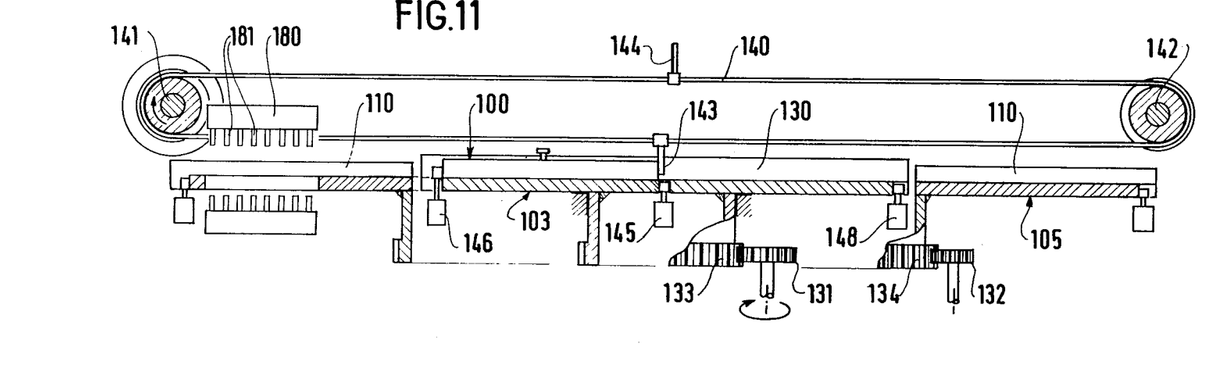
Figure 12:
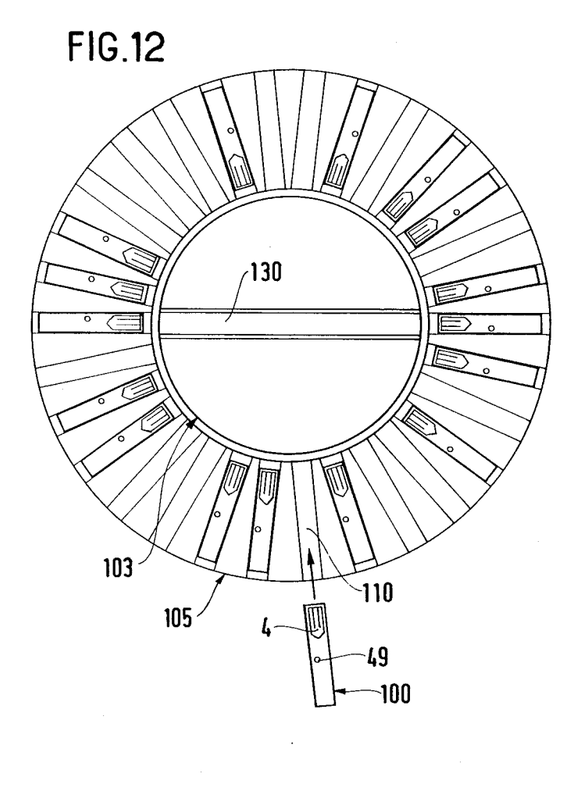
FIGS. 12 to 17 are diagrammatic plan views of the FIG. 1 apparatus during different stages of the method in accordance with the invention.
Figure 13:
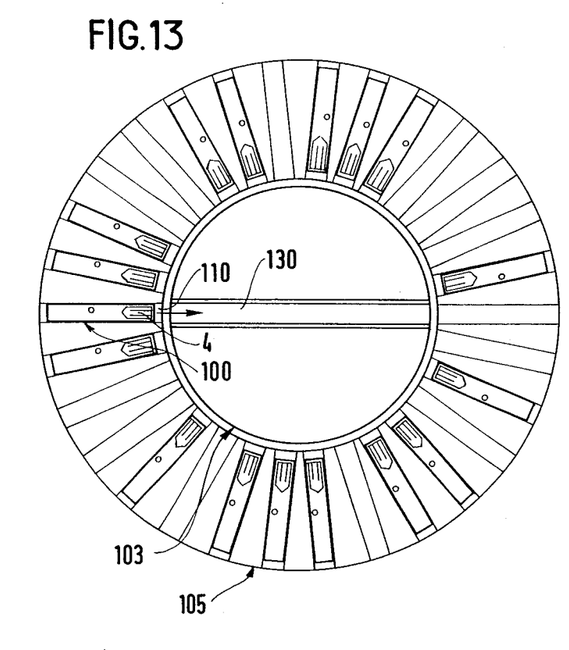
Figure 16:
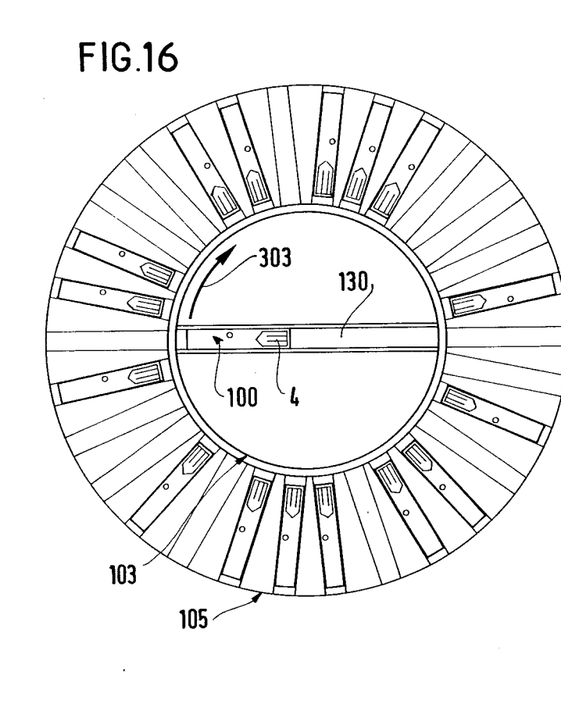
Figure 26:
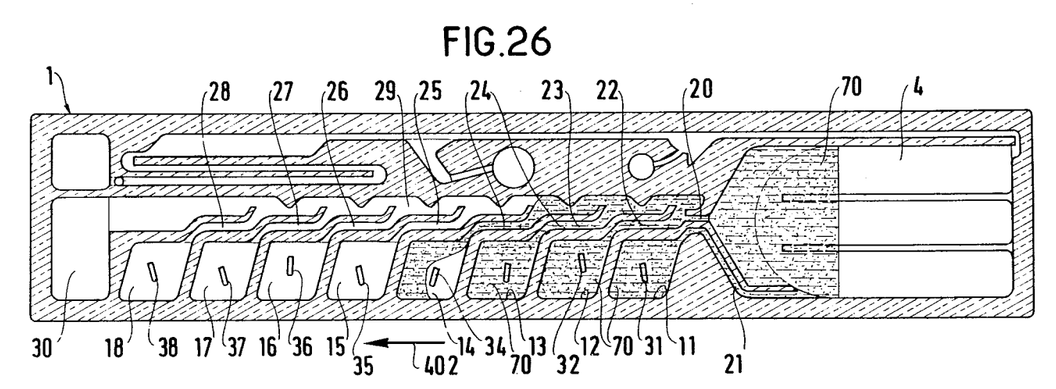
FIGS. 26 and 27 are views analogous to FIG. 20, and show the stage of the method as illustrated in FIG. 16.

Once the mixture 70 is ready, the strip 100 is returned by movement of the finger 143 to the first position which it occupied in the g roove 130 of the turntable 103 (see FIGS. 11 and 16). It is held in place by the peg 146. It is then subjected to a third centrifuging operation indicated diagrammatically by arrow 303. The resulting distribution of liquid appears in FIGS. 26 and 27, with centrifugal force being indicated by arrow 403. The liquid 70 is expelled from the mixing vat 4 via capillary duct 21 towards the vat 11 and via capillary ducts 20 towards the other vats 12 to 18 by means of the capillary ducts 22 to 28 and the powerflow duct 29.

Figure 17:
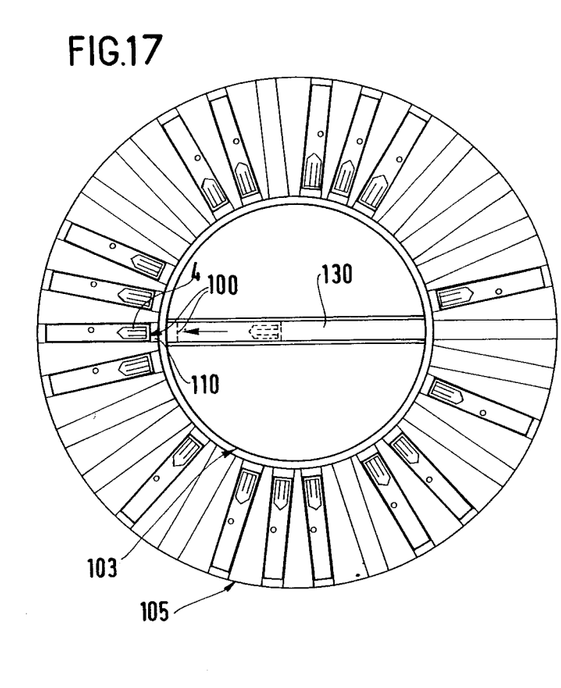
Figure 27:
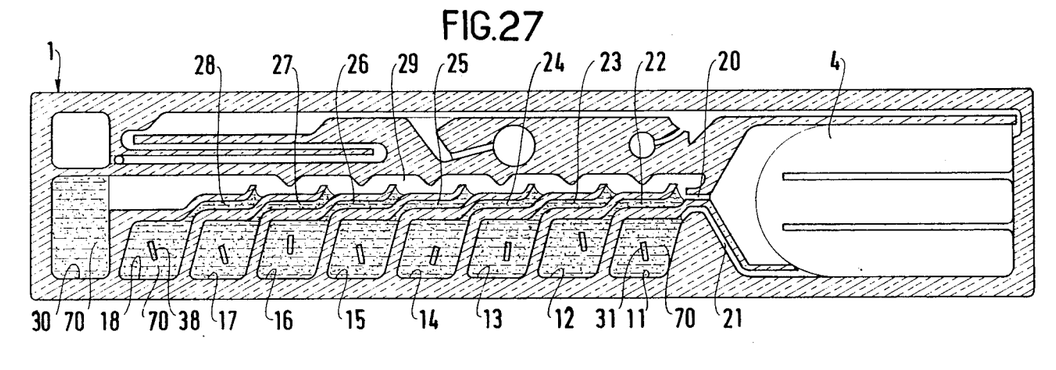

The final, rest state of the strip 100 is shown in FIG. 27 and it can be seen that the reaction vats 11 to 18 and the associated capillary ducts 22 to 28 are filled with the mixed liquid 70, as is the overflow vat 30. Reactions with the reagents 31 to 38 can then take place. As indicated in FIG. 17, the strip 100 may return to its housing 110 in the ring 105. As the ring rotates, the eight reaction vats pass beneath the eight read heads 181 of the photometer 180 (see FIG. 8).

The photometer performs simultaneous measurements which are transmitted to the control unit which interprets the results and which prints them out on a printer once the reactions have terminated.

The method in accordance with the invention is thus very simple to use and may be performed by medial practitioners themselves in their consulting rooms or offices. Different strips containing different reagents are made available to practitioners. Reference strips may also be prepared ready for use.

Naturally the invention is not limited to the embodiment described above, any of the means used therein may be replaced by equivalent means without going beyond the scope of the claims.

I claim:

1. A conditioning strip for performing medical analyses on a sample of liquid and using dry reagents, said strip being constituted by a container and a lid made of transparent plastic material, means defining an opening in said lid, a stopper for closing said opening, the container having longitudinal side walls and being compartmented in order to form, a receptacle for said liquid sample, said receptacle being in communication with said opening through said lid, a calibrated cell, a capillary duct connecting said receptacle to said calibrated cell, an overflow chamber, means connecting said calibrated cell to said overflow chamber;

a diluent tank for containing a diluent liquid situated beneath said calibrated cell and communicating via an inlet orifice within said container, said inlet orifice being closed by said lid; a mixing vat situated at one end of said strip and communicating via respective capillary ducts with said calibrated cell and with said diluent tank, all of said above-mentioned capillary ducts being parallel to the longitudinal side walls of said container;

a series of reaction vats along one of said container longitudinal side walls, for containing respective solid reagents, and said reaction vats being connected via respective capillary ducts to a common duct in communication via capillary duct, with said mixing vat and acting as an overflow duct and terminating in a common overflow vat.

2. A conditioning strip according to claim 1, wherein said container is in the form of a one-piece molding together with a bottom wall, said one-piece molding defining, together with said lid, said sample receptacle, said calibrated cell and its associated overflow chamber, said mixing vats, said reaction vats, and said sets of capillary ducts, the bottom wall of said container including a cavity which, together with said bottom wall, defines said diluent tank.

3. A conditioning strip according to claim 1 or 2, wherein said reactions vats contain respective reagents in the form of pellets or of freeze-dried material, and wherein said diluent tank contains a quantity of diluent.

* * * * *